United States Patent [19]

Lee et al.

[11] Patent Number: 5,032,232

[45] Date of Patent: Jul. 16, 1991

[54] EXTRACTIVE DISTILLATION OF HYDROCARBON MIXTURES

[75] Inventors: Fu-Ming Lee; Ronald E. Brown; Marvin M. Johnson, all of Bartlesville, Okla.

[73] Assignee: Phillips Petroleum Company, Bartlesville, Okla.

[21] Appl. No.: 606,690

[22] Filed: Oct. 31, 1990

[51] Int. Cl.$^5$ .............................................. B01D 3/40
[52] U.S. Cl. ...................................... 203/51; 203/56; 203/58; 203/64; 585/807; 585/857; 585/860; 585/865
[58] Field of Search ..................... 203/51, 56, 58, 64; 585/804-807, 811, 857, 860, 865, 833

[56] References Cited

U.S. PATENT DOCUMENTS

| | | | |
|---|---|---|---|
| 2,508,723 | 5/1950 | Mayland et al. | 585/866 |
| 2,891,894 | 6/1959 | Cier et al. | 203/60 |
| 3,114,783 | 12/1963 | Butler et al. | 203/55 |
| 3,349,009 | 10/1967 | Ruehlen | 203/67 |
| 3,431,199 | 3/1969 | Reni et al. | 208/325 |
| 4,053,369 | 10/1977 | Cines | 203/52 |
| 4,081,332 | 3/1978 | Mein | 203/51 |
| 4,349,416 | 9/1982 | Brandt et al. | 203/19 |
| 4,363,704 | 12/1982 | Berg | 203/58 |
| 4,401,517 | 8/1983 | Lee | 203/53 |
| 4,514,262 | 4/1985 | Berg | 203/51 |
| 4,676,874 | 6/1987 | Berg et al. | 203/51 |
| 4,921,581 | 5/1990 | Lee et al. | 203/56 |
| 4,944,849 | 7/1990 | Lee | 203/55 |
| 4,948,470 | 8/1990 | Lee | 203/51 |
| 4,948,472 | 8/1990 | Lee et al. | 203/55 |
| 4,954,224 | 9/1990 | Brown et al. | 203/51 |
| 4,955,468 | 9/1990 | Lee | 203/53 |
| 4,956,476 | 9/1990 | Eastman et al. | 548/552 |

OTHER PUBLICATIONS

"Handbook of Separation Techniques for Chemical Engineers", by Paul Schweitzer, McGraw-Hill, 1979, pp. 1-135 to 1-143.
"Extractive Distillation Saves Energy", by Ian Sucksmith, Chemical Engineering, June 28, 1982, pp. 91-95.
"Perry's Chemical Engineers' Handbook", Sixth Edition, McGraw-Hill, 1984, pp. 13-53 to 13-57.

Primary Examiner—Virginia Manoharan
Attorney, Agent, or Firm—K. K. Brandes

[57] ABSTRACT

Extractive distillation processes for separating aromatic hydrocarbon(s) or cycloalkane(s) or alkene(s) from close-boiling alkane(s) are carried out with a solvent including at least one N-alkyl-2-thiopyrrolidone compound, preferably N-methyl-2-thiopyrrolidone. Optionally, the solvent additionally contains a cosolvent, preferably tetraethylene glycol or N-($\beta$-mercaptoethyl)-2-pyrrolidone or unsubstituted sulfolane.

24 Claims, 1 Drawing Sheet

EXTRACTIVE DISTILLATION OF HYDROCARBON MIXTURES

BACKGROUND OF THE INVENTION

In one aspect, this invention relates to the separation of aromatic hydrocarbons from close-boiling alkanes (paraffins) by extractive distillation. In another aspect, this invention relates to the separation of cycloalkanes (naphthenes) from alkanes by extractive distillation. In a further aspect, this invention relates to the separation of alkenes (monoolefins) from alkanes by extractive distillation.

Extractive distillation is a well known technique for separating mixtures of components having a relative volatility close to unity (i.e., having nearly equal volatility and having nearly the same boiling point). It is difficult to separate the components of such mixtures by conventional fractional distillation. In extractive distillation, a solvent is introduced into a distillation column above the entry point of the feed mixture which is to be separated. The solvent affects the volatility of the higher boiling feed component(s) sufficiently to facilitate the separation of the various feed components by distillation and exits with the bottoms fraction, as has been described in the article entitled "Extractive Distillation Saves Energy" by Ian Sucksmith, Chemical Engineering, June 28, 1982, pages 91-95. Other literature sources on extractive distillation techniques include the "Handbook of Separation Techniques for Chemical Engineers" by Philip A. Schweitzer, McGraw-Hill Book Company, 1979, pages 1-135 to 1-143; Perry's Chemical Engineers Handbook, 6th Edition, McGraw-Hill Book Company, 1984, pages 13-53 to 13-57, and U.S. Pat. No. 4,921,581.

Even though the separation of various hydrocarbons, such as aromatics or cycloalkanes, from other close-boiling hydrocarbons, such as paraffins, by extractive distillation is known, there is an ever present need to develop novel solvent systems which exhibit advantages (such as higher selectivity) over known solvents in the extractive distillation of mixtures of close-boiling hydrocarbons. In particular, it is highly desirable to develop improved extractive distillation processes for separating aromatics or cycloalkanes or alkenes from close-boiling alkanes at high selectivity.

SUMMARY OF THE INVENTION

It is an object of this invention to provide a process for separating aromatic hydrocarbons from close-boiling alkanes by extractive distillation. It is another object of this invention to provide a process for separating cycloalkanes from close-boiling alkanes by extractive distillation. It is a further objective of this invention to provide a process for separating alkenes and from close-boiling alkanes by extractive distillation. Other objects and advantages will be apparent from the detailed description of the invention and the appended claims.

In accordance with this invention, a process for separating at least one aromatic hydrocarbon containing 6-12 carbon atoms per molecule from at least one close boiling alkane, i.e., one alkane or a plurality of alkanes having nearly the same boiling point at atmospheric pressure conditions as the at least one aromatic hydrocarbon, by extractive distillation of a feed comprising (preferably consisting essentially of) said at least one aromatic hydrocarbon and said at least one alkane employs a solvent comprising (preferably consisting essentially of) at least one N-alkyl-2-thiopyrrolidone compound, wherein the alkyl group contains 1-3 carbon atoms; preferably N-methyl-2-thiopyrrolidone.

Also in accordance with this invention, a process for separating at least one cycloalkane (naphthene) containing 5-10 carbon atoms per molecule from at least one close-boiling alkane, i.e., one alkane or a plurality of alkanes having nearly the same boiling point at atmospheric pressure conditions as the at least one cycloalkane, by extractive distillation of a feed comprising (preferably consisting essentially of) said at least one cycloalkane and said at least one alkane, employs a solvent (also referred to as extractant or entrainer) comprising (preferably consisting essentially of) at least one N-alkyl-2-thiopyrrolidone compound, wherein the alkyl group contains 1-3 carbon atoms; preferably N-methyl-2-thiopyrrolidone.

Further in accordance with this invention, a process for separating at least one alkene (monoolefin) containing 4-10 carbon atoms per molecule from at least one close-boiling alkane, i.e., one alkane or a plurality of alkanes having nearly the same boiling point at atmospheric pressure conditions as the at least one alkene, by extractive distillation of a feed comprising (preferably consisting essentially of) said at least one alkene and said at least one alkane, employs a solvent comprising (preferably consisting essentially of) at least one N-alkyl-2-thiopyrrolidone compound, wherein the alkyl group contains 1-3 carbon atoms; preferably N-methyl-2-thiopyrrolidone.

Still further in accordance with the present invention, the solvent employed in each of the above-described three extractive distillation processes comprises (preferably consists essentially of) a mixture of (a) at least one N-alkyl-2-thiopyrrolidone compound, as defined above, and (b) at least one cosolvent selected from the group consisting of ethylene glycol compounds, sulfolane compounds and N-($\beta$-mercaptoalkyl)-2-pyrrolidone compounds.

DETAILED DESCRIPTION OF THE INVENTION

Figure 1:
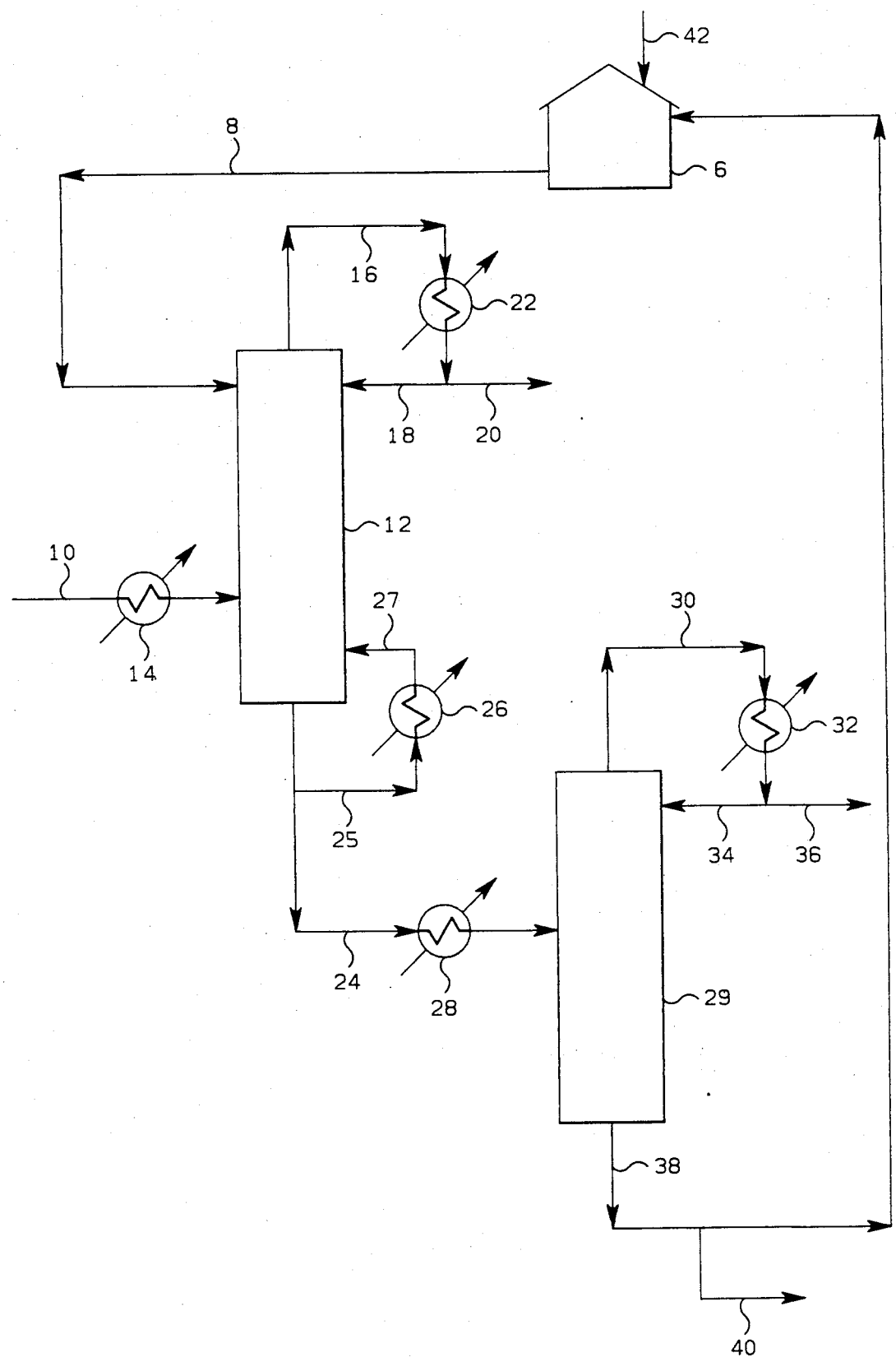
FIG. 1 illustrates the extractive distillation process of this invention.

In an extractive distillation process, an agent (called "solvent" or "extractant" or "entrainer") is added to a feed mixture of components to be separated so that the relative volatilities of the components of the mixture are changed such that a sufficient difference in volatility of the components results and effective separation by distillation becomes possible. The added solvent is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, a solvent of high selectivity is a solvent which causes great differences between the relative volatilities of the components in a mixture, and will allow for the separation of components in a mixture with fewer distillation stages, lower amount of reflux and higher product purity.

Any hydrocarbon feed which contains at least one aromatic hydrocarbon containing 6–12 carbon atoms per molecule and at least one close-boiling alkane (preferably containing 5–12 carbon atoms per molecule, more preferably branched alkane or isoparaffin) can be used in the first embodiment of this invention. Generally, the feed contains about 1–99 weight-% aromatic hydrocarbon(s) and about 1–99 weight-% alkane(s), preferably about 10–95 weight-% aromatic hydrocarbon(s) and about 5–90 weight-% alkane(s). Preferably, the feed is substantially free of cycloalkanes and alkenes. Preferably, the boiling point (at atmospheric pressure conditions, i.e., at about 1 atm.) of the aromatic hydrocarbon(s) and alkane(s) to be separated by extractive distillation is in the range of from about 80° to about 350° F., more preferably about 100°–300° F. Generally, the boiling points of the aromatic hydrocarbon(s) and the alkane(s) differ by about 0.2°–10° F. (preferably about 0.5°–5° F.), at about 1 atm.

Non-limiting examples of suitable aromatic hydrocarbons are benzene, toluene, o-xylene, m-xylene, p-xylene, ethylbenzene, 1,2,3-trimethylbenzene, 1,2,4-trimethylbenzene, 1,3,5-trimethylbenzene, 1-methyl-4-ethylbenzene, 1-methyl-4-propylbenzene, and the like and mixtures thereof. Presently preferred are benzene, toluene and the xylenes.

Non-limiting examples of suitable alkanes are n-pentane, n-hexane, 2-methylpentane, 3-methylpentane, 2,2-dimethylbutane, n-heptane, 2,2-dimethylpentane, 2,4-dimethylpentane, 3,3-dimethylpentane, 2,3-dimethylpentane, 2-methylhexane, 3-methylhexane, 2,2,3-trimethylbutane, n-octane, 2-methyloctane, n-nonane, n-decane, and the like, and mixtures thereof. Presently preferred are n-heptane and 2,2-dimethylbutane.

Any hydrocarbon feed which contains at least one cycloalkane (naphthene) containing 5–10 carbon atoms per molecule and at least one close-boiling alkane (preferably containing 5–10 carbon atoms per molecule, more preferably branched alkane or isoparaffin) can be used in the second embodiment of this invention. Generally, the feed contains about 1–99 weight-% cycloalkane(s) and about 1–99 weight-% alkane(s), preferably about 10–95 weight-% cycloalkane(s) and about 5–90 weight-% alkane(s). Preferably, the feed is substantially free of aromatic hydrocarbons and alkenes. Preferably, the boiling point (at atmospheric pressure conditions, i.e., at about 1 atm.) of the cycloalkane(s) and alkane(s) to be separated by extractive distillation is in the range of from about 80° to about 350° F., more preferably about 100°–300° F. Generally, the boiling points of the cycloalkane(s) and the alkane(s) differ by about 0.2°–10° F. (preferably about 0.5°–5° F.), at about 1 atm.

Non-limiting examples of suitable cycloalkanes are cyclopentane, cyclohexane, methylcyclopentane, cycloheptane, 1,1-dimethylcyclopentane, 1,2-dimethylcyclopentane, 1,3-dimethylcyclopentane, ethylcyclopentane, methylcyclohexane, 1,1-dimethylcyclohexane, 1,2-dimethylcyclohexane, 1,3-dimethylcyclohexane, ethylcyclohexane, cyclooctane, and the like, and mixtures thereof. Presently preferred are cyclopentane and cyclohexane. Examples of suitable alkanes are listed above.

Any hydrocarbon feed which contains at least one alkene containing 4–10 carbon atoms per molecule and at least one close-boiling alkane (preferably containing 4–10 carbon atoms per molecule, more preferably branched alkane or isoparaffin) can be used in the third embodiment of this invention. Generally, the feed contains about 1–99 weight-% alkene(s) and about 1–99 weight-% alkane(s), preferably about 10–95 weight-% alkene(s) and about 5–90 weight-% alkane(s). Preferably, the feed is substantially free of aromatic hydrocarbons and cycloalkanes. Preferably, the boiling point (at atmospheric pressure conditions, i.e., at about 1 atm.) of the alkene(s) and alkane(s) to be separated by extractive distillation is in the range of from about 20° to about 350° F., more preferably about 100°–300° F. Generally, the boiling points of the alkene(s) and the alkane(s) differ by about 0.2°–10° F. (preferably about 0.5°–5° F.), at about 1 atm.

Non-limiting examples of suitable alkenes are 1-butene, 2-butene, 2-methylpropene (isobutene), 1-pentene, 2-pentene, 2-methyl-1-butene, 1-hexene, 2-hexene, 3-hexene, 2-methyl-1-pentene, 3-methyl-2-pentene, 2-methyl-3-pentene, 1-heptene, 2-heptene, 3-heptene, 2-methyl-1-hexene, 3-methyl-1-hexene, 2-methyl-2-hexene, 2-methyl-3-hexene, 1-octene, 2-octene, 3-octene, 2-methyl-1-heptene, 3-methyl-1-heptene, 2-methyl-2-heptene, 2-methyl-3-heptene, 2,2-dimethyl-1-hexene, 1-nonene, 1-docene, and the like, and mixtures thereof. Presently preferred is cis-2-heptene. Suitable alkanes include those listed above and also n-butane and isobutane.

The structural formula of the N-alkyl-2-thiopyrrolidone compound which is used solvent in the extractive distillation processes of this invention is

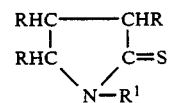

wherein each R can be H or the methyl group, and $R^1$ can be a methyl, ethyl or propyl group. Preferably, each R is H, and $R^1$ is the methyl group, i.e., the preferred compound is unsubstituted N-methyl-2-thiopyrrolidone, also referred to as N-methylpyrrolidine-2-thione, which can be prepared by any suitable method, e.g., by a catalytic reaction of N-methyl-2-pyrrolidone with $H_2S$, as has been described in U.S. Pat. No. 4,956,476.

In other preferred embodiments of the extractive distillation processes of this invention, the solvent comprises (more preferably consists essentially of) (a) N-methyl-2-thiopyrrolidone and (b) ethylene glycol or diethylene glycol or triethylene glycol or tetraethylene glycol or cyclotetramethylene sulfone (unsubstituted sulfolane) or N-(β-mercaptoethyl)-2-pyrrolidone or mixtures of two or more of these cosolvent compounds. It is within the scope of this invention (yet presently not preferred) to employ as cosolvent (b) methyl-substituted ethylene glycol compounds, or methyl-substituted sulfones, or N-mercaptoalkyl-2-pyrrolidones wherein the alkyl group contains 1 or 3–5 carbon atoms, or water, or mixtures thereof. Presently more preferred cosolvents (b) are tetraethylene glycol or unsubstituted sulfolane or N-(β-mercaptoethyl)-2-pyrrolidone.

Any suitable weight ratio of component (a) to component (b) in the solvent (also called extractant) of this invention can be employed in the extractive distillation process of this invention. Generally, the weight ratio of component (a) to component (b) is in the range of from about 0.1:1 to about 20:1, preferably from about 0.2:1 to about 5:1.

Any suitable weight ratio of the solvent to the hydrocarbon containing feed mixture can be employed in each of the extractive distillation processes of this invention. Generally, the solvent to feed weight ratio is in the range of from about 0.5:1 to about 50:1, preferably from about 1:1 to about 20:1, and more preferably from about 5:1 to about 9:1.

Any suitable reflux ratio (i.e., the weight ratio of the portion of condensed vapor which is returned to the distillation column to the portion of condensed vapor which is withdrawn as distillate) can be employed in the processes of this invention. Generally the reflux ratio is in the range of from about 0.1:1 to about 100:1, preferably in the range of from about 0.5:1 to about 50:1, more preferably in the range of from about 1:1 to about 40:1.

Any suitable feed entry location can be selected. Generally the feed entry location is in the range of from about 2 to about 70 percent of the total height of the packed or trayed column, measured upward from the bottom of the column, preferably in the range of from about 5 to about 60 percent, more preferably in the range of from about 7 to about 70 percent.

Any suitable solvent entry location can be selected. Generally the solvent entry location is in the range of from about 50 to about 99 percent of the total height of the packed or trayed column (i.e., within the upper half of the column), preferably in the range of from about 70 to about 99 percent, more preferably in the range of from about 80 to about 99 percent.

Any suitable temperature in the reboiler vessel (containing primarily the higher boiling feed components and the solvent) can be employed. The temperature is generally in the range of from about 100° to about 400° F., preferably in the range of from about 150° to about 320° F. The extractive distillation column is generally heated (more near the bottom, and less near the top). Generally, the temperature at the top of the column where the vapor exits into the condenser is in the range of from about 100° to about 300° F., preferably in the range of from about 150° to about 250° F. Solvent and feed are generally preheated (generally to a temperature close to the column temperature of the corresponding entry point) before they are introduced into the packed column. Any suitable pressure can be employed during the extractive distillation. Generally the pressure is about 5 to about 100 psig, preferably about 8 to about 20 psig.

Depending on the feed being used, the overhead distillate product (withdrawn from the top of the column) contains a smaller volume percentage of aromatic hydrocarbon(s) or cycloalkane(s) or alkene(s) than the feed and a larger volume percentage of alkane(s) than the feed; whereas the bottoms product (a portion of which can be reheated and recycled to the lower portion of the column) contains a larger volume percentage of aromatic hydrocarbon(s) or cycloalkane(s) or alkene(s) than the feed and a smaller volume percentage of alkane(s) than the feed. Furthermore, the bottoms product contains essentially all of the added solvent, which can be separated from the other bottoms product components by distillation or other suitable separating means and then be recycled to the extractive distillation column.

Any suitable total column height, packed column height, column diameter and number of trays in the extraction distillation column can be employed. The exact dimensions and column designs depend on the scale of the operation, the exact feed composition, the exact solvent composition, the desired recovery and degree of purity of the various products, and the like, and can be determined by those having ordinary skills in the art.

The invention can be better understood by reference to FIG. 1 and the following description of a preferred embodiment of the invention. A feed mixture comprising aromatic hydrocarbon(s) and alkane(s) is introduced through conduit 10 to a fractionation zone such as multi-stage distillation column 12. The temperature of the feed mixture flowing through conduit 10 can be adjusted as needed by controlling heat exchanger 14 so as to add heat to or remove heat from the feed mixture. Solvent from solvent storage 6 is introduced to distillation column 12 through conduit 8, and an overhead stream enriched in alkane(s) is withdrawn from an upper portion of distillation column 12 through conduit 16. This overhead stream can be completely passed to storage or to other processing units or, as is often the case, the overhead stream can be partially or totally condensed, with a portion thereof being returned to the fractionation zone as reflux. The overhead stream passing through conduit 16 is condensed in condenser 22 to yield a condensed overhead stream. A portion of the condensed overhead stream can be returned to distillation column 12 as reflux through conduit 18, while the remainder of the condensed overhead stream is yielded as product or passed to other processing units through conduit 20.

A bottoms stream is withdrawn from a lower portion of the fractionation zone represented by distillation column 12 through conduit 24. A portion of the fluids withdrawn from the bottom of distillation column 12 may be heated and returned to distillation column 12. For example, a portion of the bottom products stream can be withdrawn through conduit 25, heated in reboiler 26 and then passed back to a lower portion of distillation column 12 through conduit 27.

Operating conditions in heat exchanger 14, condenser 22 and reboiler 26 can be controlled and interfaced with solvent flow through conduit 8, feed mixture flow through conduit 10, reflux flow through conduit 18 and bottom stream flow through conduit 24 such that the feed mixture introduced into distillation column 12 will be fractionated to yield an overhead stream which is enriched in alkane(s) and a bottoms stream predominantly comprising the aromatic hydrocarbon(s) and the solvent.

The bottoms stream passing through conduit 24 can be passed to storage, used in other processes or, preferably, passed to another fractionation zone, such as distillation column 29. Any adjustments to the temperature of the bottom stream passing through conduit 24 necessary for efficient fractionation in distillation column 29 can be made by appropriately adjusting heat exchanger 28. An overhead stream predominantly comprising aromatic hydrocarbon(s) is withdrawn from an upper portion of distillation column 29 through conduit 30. This overhead stream can be at least partially condensed in condenser 32. A portion of the overhead stream withdrawn from condenser 32 can be returned through conduit 34 as reflux for distillation column 29, with the remainder of the overhead stream being withdrawn as product, i.e., aromatic hydrocarbon(s) of high purity (preferably higher than 95%), through conduit 36.

A bottoms stream predominantly comprising the solvent is withdrawn from a lower portion of distillation column 29 through conduit 38. A portion of this bottoms stream is preferably routed back to solvent storage 6 and then recycled to distillation column 12, while another portion of the bottoms stream is heated in a reboiler (not shown) and returned to the lower portion of column 29. From time to time, impurities which may build up in the solvent can be removed from the system by removing a small purge stream through conduit 40. Solvent lost through the purge stream or through other processing losses may be made up by a makeup stream passing through conduit 42 and into solvent storage tank 6.

The above description of FIG. 1 can be applied to another preferred embodiment of this invention, namely the separation of cycloalkane(s) from close-boiling alkane(s), by substituting the term "cycloalkane(s)" for the term "aromatic hydrocarbon(s)" wherever it occurs in the above description. The above description of FIG. 1 can also be applied to a further preferred embodiment of this invention, namely the separation of alkene(s) from close boiling alkane(s), by substituting the term "alkene(s)" for the term "aromatic hydrocarbon(s)" wherever it occurs in the above description.

The following examples are presented to further illustrate the invention and are not to be considered unduly limiting the scope of this invention.

EXAMPLE I

This example demonstrates the superiority of N-methyl-2-thiopyrrolidone (NMTP, also referred to as N-methylpyrrolidine-2-thione) over N-methyl-2-pyrrolidone (NMP) in the extractive distillation of a feed which contains an aromatic hydrocarbon and a close-boiling alkane.

To a hydrocarbon mixture of 50 weight-% toluene and 50 weight-% n-heptane was added an extractive solvent (either NMTP or NMP) at various solvent:feed weight ratios. The total mixture (including the extractive solvent) was heated under reflux conditions for about 20-30 minutes in a distillation flask equipped with a reflux condenser. Then a small sample was withdrawn by means of a septum from the flask containing the liquid phase of the equilibrium system, and a sample of the condensed vapor was withdrawn by means of a septum located just below the reflux condenser. Both samples were analyzed by means of a chromatograph, and the mole fractions of toluene and n-heptane in the liquid phase and in the vapor phase were determined. The relative volatility R was calculated as follows:

$$R = \frac{Y1/Y2}{X1/X2} = \frac{Y1/X1}{Y2/X2},$$

wherein Y1 and Y2 are the mole fractions of n-heptane and toluene, respectively, in the vapor phase; and X1 and X2 are the mole fractions of n-heptane and toluene, respectively, in the liquid phase. Test results are summarized in Table I.

TABLE I

| Solvent:Feed Weight Ratio | Added Solvent | Relative Volatility R |
|---|---|---|
| 1:1 | NMTP | 2.8 |
| 1:1 | NMP | 2.6 |
| 3:1 | NMTP | 3.9 |
| 3:1 | NMP | 3.2 |
| 5:1 | NMTP | 4.2 |
| 5:1 | NMP | 3.4 |

Based on the test data in Table I, it is concluded that N-methyl-2-thiopyrrolidone (NMTP) would be more effective than N-methyl-2-pyrrolidone (NMP) as solvent in the extractive distillation of feeds comprising aromatic hydrocarbon(s), in particular toluene, and close-boiling alkane(s), in particular n-heptane.

EXAMPLE II

This example illustrates the use of various solvent mixtures containing N-methyl-2-thiopyrrolidone (NMTP) in the extractive distillation of a feed which contains an aromatic hydrocarbon and a close-boiling alkane.

All tests were carried out in accordance with the procedure described in Example I, employing the same feed but using solvent mixtures. Test results for preferred solvent:feed ratios are summarized in Table II.

TABLE II

| Solvent:Feed Weight Ratio | Added Solvent | Relative Volatility R |
|---|---|---|
| 3:1 | NMTP | 3.9[1] |
| 3:1 | NMTP + TEG[2] | 3.8 |
| 3:1 | NMTP + NMEP[3] | 4.0 |
| 3:1 | NMTP + Sulfolane[4] | 4.2 |
| 3:1 | NMTP + Sulfolane[5] | 4.4 |
| 3:1 | NMTP + Sulfolane[6] | 3.9 |
| 5:1 | NMTP | 4.2[1] |
| 5:1 | NMTP + TEG[2] | 4.6 |
| 5:1 | NMTP + NMEP[3] | 4.8 |
| 5:1 | NMTP + Sulfolane[4] | 4.8 |
| 5:1 | NMTP + Sulfolane[5] | 5.2 |
| 5:1 | NMTP + Sulfolane[6] | 5.3 |

[1]from Table I
[2]50 weight % N-methyl-2-thiopyrrolidone + 50 weight % tetraethylene glycol
[3]50 weight % N-methyl-2-thiopyrrolidone + 50 weight % N-(β-mercaptoethyl)-2-pyrrolidone
[4]75 weight % N-methyl-2-thiopyrrolidone + 25 weight % unsubstituted sulfolane (cyclotetramethylene sulfone)
[5]50 weight % N-methyl-2-thiopyrrolidone + 50 weight % unsubstituted sulfolane
[6]25 weight % N-methyl-2-thiopyrrolidone + 75 weight % unsubstituted Test results in Table II indicate that the tested mixtures would generally be more effective than N-methyl-2-thiopyrrolidone alone as solvent in the extractive distillation of feeds comprising aromatic hydrocarbon(s) and alkane(s), in particular toluene and n-heptane. Solvent mixtures comprising NMTP and sulfonlane are particularly preferred. Additional test results (not included in Table II) showed that the relative volatility attained with sulfolane alone was less than the relative volatility attained with the above-described three NMTP+sulfonlane mixtures, at solvent: feed weight-ratios of 3:1 and 5:1.

EXAMPLE III

This example demonstrates the superiority of N-methyl-2-thiopyrrolidone (NMTP) over N-methyl-2-pyrrolidone (NMP) in the extractive distillation of a feed which contains a cycloalkane and a close-boiling alkane.

All tests were carried out in accordance with the procedure described in Example I, except that a feed containing 50 weight-% cyclopentane and 50 weight-% 2,2-dimethylbutane was used. The mole fractions of these two hydrocarbons in the liquid phase and in the vapor phase were determined by means of a gas chromatograph. The relative volatility $R^1$ was calculated as follows:

$$R^1 = \frac{Y3/Y4}{X3/X4} = \frac{Y3/X3}{Y4/X4},$$

where Y3 and Y4 are the mole fractions of 2,2-dimethylbutane and cyclopentane, respectively, in the vapor phase; and X3 and X4 are the mole fractions of 2,2-dimethylbutane and cyclopentane, respectively, in the liquid phase. Test results are summarized in Table III.

| Solvent:Feed Weight ratio | Added Solvent | Relative Volatility $R^1$ |
|---|---|---|
| 1:1 | NMTP | 1.1 |
| 1:1 | NMP | 1.2 |
| 3:1 | NMTP | 1.4 |
| 3:1 | NMP | 1.4 |
| 5:1 | NMTP | 1.7 |
| 5:1 | NMP | 1.4 |
| 7:1 | NMTP | 1.8 |
| 7:1 | NMP | 1.3 |
| 9:1 | NMTP | 1.8 |
| 9:1 | NMP | 1.3 |

Based on the test data in Table III, it is concluded that NMTP would be more effective than NMP as solvent in the extractive distillation of a feed mixture comprising cycloalkane(s) and alkane(s), in particular for a cyclopentane/2,2-dimethylbutane feed at a solvent: feed weight ratio of about 5–9:1.

EXAMPLE IV

This example illustrates that use of various solvent mixtures containing N-methyl-2-thiopyrrolidone (NMTP) in the extractive distillation of a feed which contains a cycloalkane and a close-boiling alkane.

All tests were carried out in accordance with the procedure described in Example III, employing the same feed but using different solvents. Test results for the preferred solvent: feed ratios of 5–9:1 are summarized in Table IV.

TABLE IV

| Solvent:Feed Weight Ratio | Added Solvent | Relative Volatility $R^1$ |
|---|---|---|
| 5:1 | NMTP + TEG$^1$ | 1.3 |
| 5:1 | TEG | 1.2 |
| 5:1 | NMTP + NMEP$^2$ | 1.6 |
| 5:1 | NMEP | 1.5 |
| 5:1 | NMTP + Sulfolane$^3$ | 1.4 |
| 5:1 | NMTP + Sulfolane$^4$ | 1.3 |
| 5:1 | Sulfolane | 1.1 |
| 7:1 | NMTP + TEG$^1$ | 1.4 |
| 7:1 | TEG | 1.2 |
| 7:1 | NMTP + NMEP$^2$ | 1.8 |
| 7:1 | NMEP | 1.7 |
| 7:1 | NMTP + Sulfolane$^3$ | 1.5 |
| 7:1 | NMTP + Sulfolane$^4$ | 1.4 |
| 7:1 | Sulfolane | 1.2 |
| 9:1 | NMTP + TEG$^1$ | 1.5 |
| 9:1 | TEG | 1.3 |
| 9:1 | NMTP + NMEP$^2$ | 1.9 |
| 9:1 | NMEP | 1.8 |
| 9:1 | NMTP + Sulfolane | 1.7 |
| 9:1 | NMTP + Sulfolane$^4$ | 1.5 |
| 9:1 | Sulfolane | 1.3 |

[1] 25 weight % N-methyl-2-thiopyrrolidone + 75 weight % tetraethylene glycol
[2] 50 weight % N-methyl-2-thiopyrrolidone + 50 weight % of N-(β-mercaptoethyl)-2-pyrrolidone
[3] 50 weight % N-methyl-2-thiopyrrolidone + 50 weight % unsubstituted sulfolane
[4] 25 weight % N-methyl-2-thiopyrrolidone + 75 weight % unsubstituted sulfolane Based on the test data in Table IV, it is concluded that mixtures of (a) N-methyl-2-thiopyrrolidone (NMTP) and (b) tetraethylene glycol (TEG) or N-(β-mercaptoethyl) pyrrolidone (NMEP) or sulfolane would be more effective as solvents in the extractive distillation of cycloalkane/alkane feeds, in particular cyclopentane/2,2-dimethylbutane feeds than TEG or NMEP of sulfolane alone.

EXAMPLE V

This example demonstrates the superiority of N-methyl-2-thiopyrrolidone (NMTP) over N-methyl-2-pyrrolidone (NMP) in the extractive distillation of a feed which contains a monoolefin (alkene) and a close-boiling paraffin (alkane).

All tests were carried out in accordance with the procedure described in Example I, except that a feed containing 50 weight-% cis-2-heptene and 50 weight-% n-heptane was used. The mole fractions of the two hydrocarbons in the liquid phase and in the vapor phase were determined by means of a gas chromatograph. The relative volatility $R^2$ was calculated as follows:

$$R^2 = \frac{Y5/Y6}{X5/X6} = \frac{Y5/X5}{Y6/X6},$$

wherein Y5 and Y6 are mole fractions of n-heptane and cis-2-heptene, respectively, in the vapor phase; and X5 and X6 are the mole fractions of n-heptane and cis-2-heptene, respectively, in the liquid phase. Test results are summarized in Table V.

TABLE V

| Solvent:Feed Weight Ratio | Added Solvent | Relative Volatility $R^2$ |
|---|---|---|
| 1:1 | NMTP | 1.1 |
| 1:1 | NMP | 1.2 |
| 3:1 | NMTP | 1.3 |
| 3:1 | NMP | 1.3 |
| 5:1 | NMTP | 1.4 |
| 5:1 | NMP | 1.3 |
| 7:1 | NMTP | 1.4 |
| 7:1 | NMP | 1.3 |

Test data in Table V indicate that at a solvent: feed weight ratio of 5–7:1, N-methyl-2-thiopyrrolidone (NMTP) would be slightly more effective than N-methyl-2-pyrrolidone (NMP) as solvent in the extractive distillation of an alkene/alkane feed, in particular a cis-2-heptene/n-heptane feed.

EXAMPLE VI

This example illustrates the use of various solvent mixtures containing NMTP in the extractive distillation of an alkene/alkane feed.

All tests were carried out in accordance with the procedure described in Example V, employing the same feed but using different solvents. Test results for the preferred solvent: feed ratios are summarized in Table VI.

TABLE VI

| Solvent:Feed Weight Ratio | Added Solvent | Relative Volatility $R^2$ |
|---|---|---|
| 5:1 | NMTP + TEG$^1$ | 1.2 |
| 5:1 | TEG | 1.1 |
| 5:1 | NMTP + Sulfolane$^2$ | 1.2 |
| 5:1 | Sulfolane | 1.2 |
| 7:1 | NMTP + TEG$^1$ | 1.3 |
| 7:1 | TEG | 1.1 |
| 7:1 | NMTP + Sulfolane$^2$ | 1.3 |
| 7:1 | Sulfolane | 1.2 |

[1] 50 weight % N-methyl-2-thiopyrrolidone + 50 weight % tetraethylene glycol
[2] 50 weight % N-methyl-2-thiopyrrolidone + 50 weight % unsubstituted sulfolane Test data in Table VI indicate that the two tested mixtures would generally be slightly more effective as solvent in the extractive distillation of an alkene/alkane feed than tetraethylene glycol or sulfolane alone.

Reasonable variations, modifications and adaptations for various usages and conditions can be made within the scope of the disclosure and the appended claims, without departing from the scope of this invention.

That which is claimed is:

1. A process for separating at least one aromatic hydrocarbon containing 6–12 carbon atoms per molecule from at least one close-boiling alkane by extractive distillation of a feed consisting essentially of said at least one aromatic hydrocarbon and said at least one alkane in the presence of a solvent consisting essentially of N-methyl-2-thiopyrrolidone, optionally in combination with at least one cosolvent selected from the group consisting of glycol compounds, sulfolane compounds and N-(β-mercaptoalkyl)-2-pyrrolidone compounds;

wherein said extractive distillation process produces (i) an overhead distillate product which contains a smaller volume percentage of said at least one aromatic hydrocarbon and a larger volume percentage of said at least one alkane than said feed, and (ii) a bottoms product which contains said solvent and a larger volume percentage of said at least one aromatic hydrocarbon and a smaller volume percentage of said at least one alkane than said feed; and wherein said at least one aromatic hydrocarbon is separated from said solvent and recovered from said bottoms product.

2. A process in accordance with claim 1, wherein said feed consists essentially of about 1–99 weight-% of said at least one aromatic hydrocarbon and about 1–99 weight-% of said at least one alkane.

3. A process in accordance with claim 1, wherein said at least one aromatic hydrocarbon is selected from the group consisting of benzene, toluene, o-xylene, m-xylene and p-xylene.

4. A process in accordance with claim 1, wherein said at least one alkane contains 5–12 carbon atoms per molecule.

5. A process in accordance with claim 1, wherein the weight ratio of said solvent to said feed is about 0.5:1 to about 50:1.

6. A process in accordance with claim 1, wherein said at least one cosolvent is selected from the group consisting of ethylene glycol, diethylene glycol, triethylene glycol, tetraethylene glycol, cyclotetramethylene sulfone, and N-(β-mercaptoethyl)-2-pyrrolidone.

7. A process in accordance with claim 1, wherein said at least one cosolvent is selected from the group consisting of tetraethylene glycol, cyclotetramethylene sulfone and N-(β-mercaptoethyl)-2-pyrrolidone.

8. A process in accordance with claim 7 wherein the weight ratio of N-methyl-2-thiopyrrolidone to said at least one cosolvent is in the range of about 0.1:1 to about 20:1.

9. A process for separating at least one cycloalkane containing 5–10 carbon atoms per molecule from at least one close-boiling alkane by extractive distillation of a feed consisting essentially of said at least one cycloalkane and said at least one alkane in the presence of a solvent consisting essentially of N-methyl-2-thiopyrrolidone, optionally in combination with at least one cosolvent selected from the group consisting of glycol compounds, sulfolane compounds and N-(β-mercaptoalkyl)-2-pyrrolidone compounds;

wherein said extractive distillation process produces (i) an overhead distillate product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

10. A process in accordance with claim 9, wherein said feed consists essentially of about 1–99 weight-% of said at least one cycloalkane and about 1–99 weight-% of said at least one alkane.

11. A process in accordance with claim 9, wherein said at least one cycloalkane is selected from the group consisting of cyclopentane and cyclohexane.

12. A process in accordance with claim 9, wherein said at least one alkane contains 5–10 carbon atoms per molecule.

13. A process in accordance with claim 9, wherein the weight ratio of said solvent to said feed is about 0.5:1 to about 50:1.

14. A process in accordance with claim 9, wherein said at least one cosolvent is selected from the group consisting of ethylene glycol, diethylene glycol, triethylene glycol, tetraethylene glycol, cyclotetramethylene sulfone and N-(β-mercaptoethyl)-2-pyrrolidone.

15. A process in accordance with claim 9, wherein said at least one cosolvent is selected from the group consisting of tetraethylene glycol, cyclotetramethylene sulfone and N-(β-mercaptoethyl)-2-pyrrolidone.

16. A process in accordance with claim 15, wherein the weight ratio of N-methyl-2-thiopyrrolidone to said at least one cosolvent is in the range of about 0.1:1 to about 20:1.

17. A process for separating at least one alkene containing 4–10 carbon atoms per molecule from at least one close-boiling alkane by extractive distillation of a feed consisting essentially of said at least one alkene and said at least one alkane in the presence of a solvent consisting essentially of N-methyl-2-thiopyrrolidone, optionally in combination with at least one cosolvent selected from the group consisting of glycol compounds, sulfolane compounds and N-(β-mercaptoalkyl)-2-pyrrolidone compounds;

wherein said extractive distillation process produces (i) an overhead distillate product which contains a smaller volume percentage of said at least one alkene and a larger volume percentage of said at least one alkane than said feed, and (ii) a bottoms product which contains said solvent and a larger volume percentage of said at least one alkene and a smaller volume percentage of said at least one alkane than said feed; and wherein said at least one alkene is separated from said solvent and recovered from said bottoms product.

18. A process in accordance with claim 17, wherein said feed consists initially of about 1–99 weight-% of said at least one alkene and 1–99 weight-% of said at least one alkane.

19. A process in accordance with claim 17, wherein said at least one alkene is cis-2-heptene.

20. A process in accordance with claim 17, wherein said at least one alkane contains about 4–10 carbon atoms per molecule.

21. A process in accordance with claim 17, wherein the weight ratio of said solvent to said feed is about 0.5:1 to about 50:1.

22. A process in accordance with claim 17, wherein said at least one cosolvent is selected from the group consisting of ethylene glycol, diethylene glycol, triethylene glycol, tetraethylene glycol, cyclotetramethylene sulfone, and N-(β-mercaptoethyl)-2-pyrrolidone.

23. A process in accordance with claim 17, wherein said at least one cosolvent is selected from the group consisting of tetraethylene glycol, cyclotetramethylene sulfone and N-(β-mercaptoethyl)-2-pyrrolidone.

24. A process in accordance with claim 23, wherein the weight ratio of N-methyl-2-thiopyrrolidone to said at least one cosolvent is in the range of about 0.1:1 to about 20:1.

* * * * *